(12) United States Patent
Sasaki et al.

(10) Patent No.: US 8,357,822 B2
(45) Date of Patent: Jan. 22, 2013

(54) PROCESS FOR PRODUCING HIGH-PURITY CHLOROPHOSPHITE

(75) Inventors: Kentaro Sasaki, Tokyo (JP); Katsuhiko Tsunashima, Tokyo (JP); Tadashi Saito, Tokyo (JP); Yoshifusa Hara, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 202 days.

(21) Appl. No.: 12/745,109

(22) PCT Filed: Dec. 5, 2008

(86) PCT No.: PCT/JP2008/072125
§ 371 (c)(1),
(2), (4) Date: Sep. 3, 2010

(87) PCT Pub. No.: WO2009/072591
PCT Pub. Date: Jun. 11, 2009

(65) Prior Publication Data
US 2010/0324337 A1    Dec. 23, 2010

(30) Foreign Application Priority Data
Dec. 6, 2007  (JP) .................................. 2007-315579

(51) Int. Cl.
*C07F 9/02*    (2006.01)
(52) U.S. Cl. ........................................................ 568/14
(58) Field of Classification Search .................... 568/14; 556/19; 558/140
See application file for complete search history.

(56) References Cited

U.S. PATENT DOCUMENTS
4,032,602 A    6/1977    Mazour et al.

FOREIGN PATENT DOCUMENTS
JP    61-112088 A    5/1986
JP    2-145594 A    6/1990
JP    02-145594 A    6/1990

OTHER PUBLICATIONS

Belyalov, R. U. et al.; Zhurnal Obshchei Khimii (1981), 51(1), 24-8; Reaction of phosphorous acid esters with phosphorus(III) halides.*
Ewin Richard A.; Encyclopedia of reagents for organic synthesis (available in USPTO library dated Nov. 22, 1995.*
Belyalov et al; Zhurnal Obshchei khimii, 1981, vol. 51, No. 1: 21-30 (with translation).*
International Search Report of PCT/JP2008/072125, Mailing Date of Jan. 6, 2009.

* cited by examiner

*Primary Examiner* — Johann Richter
*Assistant Examiner* — Pancham Bakshi
(74) *Attorney, Agent, or Firm* — Westerman, Hattori, Daniels & Adrian, LLP

(57)   ABSTRACT

There is provided a process capable of preventing the adhesion of a catalyst to an evaporator in a step of separating a chlorophosphite as a target substance from a reaction liquid by evaporation. The process includes a first step of allowing phosphorus trichloride and a phosphorous acid triester represented by $(RO)_3P$ to react in the presence of a catalyst having a viscosity at 80° C. of 100 mPa·s or lower to produce a chlorophosphite represented by $RO(R')PCl$, and a second step of vaporizing a reaction liquid containing the chlorophosphite obtained in the first step, in a short time, to separate the catalyst.

8 Claims, 1 Drawing Sheet

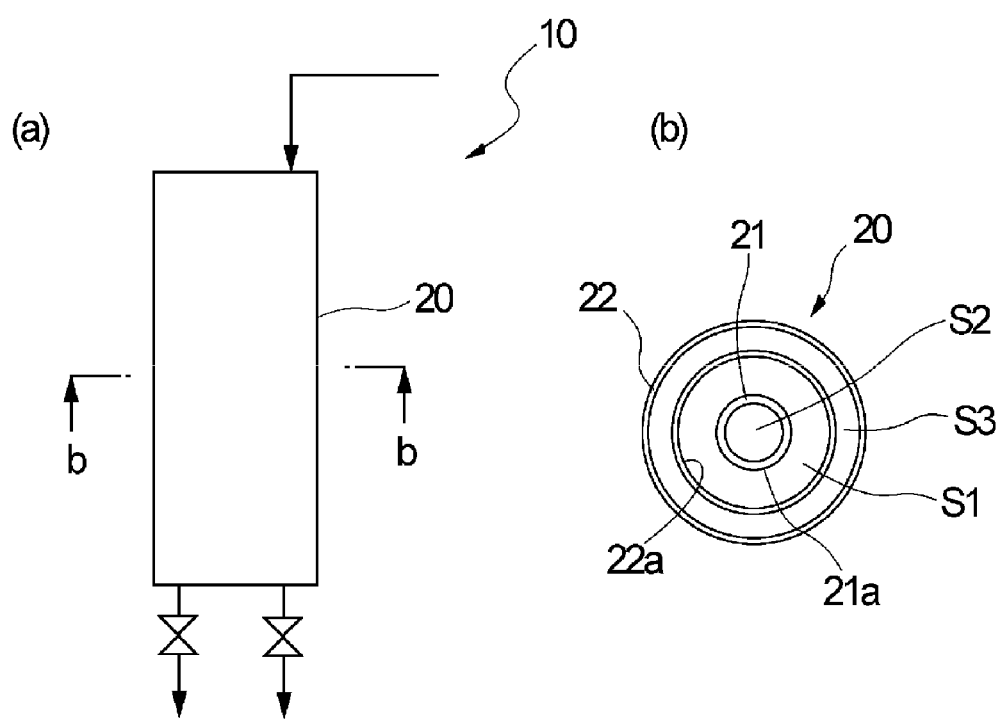

PROCESS FOR PRODUCING HIGH-PURITY CHLOROPHOSPHITE

TECHNICAL FIELD

The present invention relates to a process for producing a high-purity chlorophosphite. The chlorophosphite is a useful substance as a raw material, for example, for organophosphate agrochemicals.

BACKGROUND ART

The present applicant previously proposed a process for producing a high-purity chlorophosphite in which phosphorus trichloride and a phosphorous acid triester are allowed to react in the presence of a catalyst to produce a chlorophosphite, and a reaction liquid containing the chlorophosphite produced is separated from the catalyst in a short time (see Patent Document 1). An advantage of the process is to provide a high-purity chlorophosphite in a high yield. Another advantage of the process is that the process is capable of selectively producing a chlorophosphite and a dichlorophosphite.

In the production process described above, a reaction liquid containing a chlorophosphite is supplied to a heated inner surface of an evaporator, and is allowed to flow down in a filmy state along the inner surface to cause rapid vaporization and to cause the chlorophosphite as a target substance to evaporate and be separated from a catalyst. In this case, depending on the kind of the catalyst, the solidified catalyst is adhered in a powdery state on the inner surface of the evaporator, causing trouble in continuous production in some cases. The phenomenon also causes a decrease in the yield of the target chlorophosphite.

Further, the present applicant previously proposed the use of a quaternary phosphonium salt as a catalyst usable in the production process described above (see Patent Document 2). However, the case where this compound is used as a catalyst also causes trouble as described above in some cases.
Patent Document 1: Japanese Patent Laid-Open No. 61-112088
Patent Document 2: Japanese Patent Laid-Open No. 2-145594

DISCLOSURE OF THE INVENTION

Problems to be Solved by the Invention

Therefore, it is an object of the present invention to provide a process for producing a chlorophosphite, more improved in productivity than the conventional technologies described before.

Means for Solving the Problems

As a result of various studies to solve the problems described above, the present inventors have found that the use of a catalyst having a low viscosity as a catalyst used in production of a chlorophosphite can prevent unintended adhesion of the catalyst and can produce a high-purity chlorophosphite in a high yield.

The present invention has been achieved based on the finding described above, and provides a process for producing a high-purity chlorophosphite, the process comprising a first step of allowing phosphorus trichloride and a phosphorous acid triester represented by $(RO)_3P$ (wherein R denotes an alkyl group, a substituted alkyl group, a phenyl group or a substituted phenyl group) to react in the presence of a catalyst having a viscosity at 80° C. of 100 mPa·s or lower to produce a chlorophosphite represented by $RO(R')PCl$ (wherein R is the same as defined above, and R' denotes RO or a chlorine atom), and a second step of vaporizing a reaction liquid containing the chlorophosphite obtained in the first step, in a short time, to separate the catalyst.

BEST MODE FOR CARRYING OUT THE INVENTION

In the first step of the production process according to the present invention, phosphorus trichloride and a phosphorous acid triester represented by $(RO)_3P$ are allowed to react in the presence of a catalyst. In the phosphorous acid triester used in the reaction, R is an alkyl group, a substituted alkyl group, a phenyl group, or a substituted phenyl group. In the phosphorous acid triester represented by $(RO)_3P$, three Rs may be identical or different. The three Rs are generally identical from the viewpoint of easiness of the synthesis process.

In the phosphorous acid triester represented by $(RO)_3P$, in the case where R is an alkyl group, the alkyl group is preferably a group having 1 to 14 carbon atoms, such as a methyl group, an ethyl group, a propyl group, a butyl group, an amyl group, a hexyl group, a cyclohexyl group, an octyl group, a decyl group, a dodecyl group or a tetradecyl group, and especially preferably a group having 1 to 6 carbon atoms therein.

In the case where R is a substituted alkyl group, the substituted alkyl group includes above-mentioned alkyl groups substituted with a halogen, a cyano group, an alkoxy group, or the like.

In the case where R is a substituted phenyl group, the substituted phenyl group includes phenyl groups substituted with an alkyl group, a nitro group, a halogen, or the like.

Suitable examples of the phosphorous acid triester represented by $(RO)_3P$ include trimethyl phosphite, triethyl phosphite, tripropyl phosphite, tributyl phosphite, trioctyl phosphite and triphenyl phosphite.

In the present invention, proper regulation of feed amounts of phosphorus trichloride and a phosphorous acid triester represented by $(RO)_3P$ allows for selective production of a chlorophosphite and a dichlorophosphite. Specifically, use of preferably 1.8 to 2.2 mol of a phosphorous acid triester, and more preferably 1.85 to 2.1 mol thereof with respect to 1 mol of phosphorus trichloride can selectively provide a chlorophosphite. By contrast, use of preferably 0.45 to 0.55 mol of a phosphorous acid triester, and more preferably 0.48 to 0.52 mol thereof with respect to 1 mol of phosphorus trichloride can selectively provide a dichlorophosphite.

For reacting phosphorus trichloride and a phosphorous acid triester represented by $(RO)_3P$, a catalyst is used. The production process according to the present invention has one feature in a catalyst to be used. The catalyst used in the present invention has a viscosity at 80° C. of 100 mPa·s or lower, preferably 80 mPa·s or less, and more preferably 60 mPa·s or lower (hereinafter, if there is a saying of a viscosity, the viscosity refers to a value measured at 80° C.). Use of a catalyst having such a viscosity can prevent the unintended adhesion of the catalyst when a reaction liquid containing a chlorophosphite obtained in the first step is evaporated and separated in the second step. As a result, production of the chlorophosphite can be carried out continuously over a long time with no discontinuance, leading to an improved yield. Further, a high-purity chlorophosphite can be produced in a high yield. The lower limit of the viscosity of a catalyst is not especially limited, and the viscosity is preferably as low as possible in the range exhibiting a sufficient power as a catalyst. If the viscosity is as low as about 100 mPa·s, the production process according to the present invention can be carried out with no trouble.

In the present invention, the viscosity was measured at 80° C. under an atmosphere of nitrogen using a vibration type viscometer (VM-10A, made by CBC Co., Ltd.) calibrated with a viscosity standard liquid (made by Brookfield Engineering Laboratories, Inc.).

The catalyst used in the present invention is preferably a quaternary ammonium salt or quaternary phosphonium salt represented by the formula (1) shown below and having a viscosity equal to or lower than the value described above. Especially a quaternary ammonium salt or quaternary phosphonium salt which is a liquid at 80° C. and has a viscosity equal to or lower than the value described above is preferably used from the viewpoint of prevention of adhesion of the catalyst, and from the viewpoint that a chlorophosphite can be obtained in a high yield and with a high quality. The compounds represented by the formula (1) may be used singly or in combination of two or more.

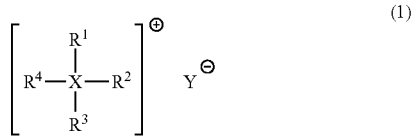

(1)

(wherein $R^1$, $R^2$, $R^3$ and $R^4$ each independently denote an alkyl group having 1 to 14 carbon atoms; X denotes N or P; and Y denotes a monovalent anion.)

In the compound represented by the formula (1), preferably, three alkyl groups of the four alkyl groups of $R^1$ to $R^4$ are the same group, and the rest one alkyl group is a group different from those, from the viewpoint of the decrease in the viscosity and the improvement of the catalytic power. In this case, if the difference in the number of carbons between the three alkyl groups and the rest one alkyl group is 2 to 10, especially 2 to 8, it is preferable because the viscosity is more decreased and the catalytic power is more enhanced. The magnitude relation between the number of carbons of the three alkyl groups and that of the rest one alkyl group is not especially limited; and there are thus a case where the number of carbons of the three alkyl groups is larger than that of the rest one alkyl group, and a case where the number of carbons of the three alkyl groups is smaller than that of the rest one alkyl group.

The anion denoted as Y in a compound represented by the formula (1) includes bis(trifluoromethylsulfonyl)imide, bis(fluorosulfonyl)imide, dicyanamide, halogens, tetrafluoroborate, hexafluorophosphate, trifluoromethanesulfonate, methanesulfonate, trifluoroacetate, thiocyanate, dimethylphosphate, diethylphosphorodithioate and amino acids.

In a compound represented by the formula (1), even if the same cation is used, the viscosity differs depending on the kind of anions. Therefore, the selection of an anion is also important from the viewpoint of decreasing the viscosity of the compound represented by the formula (1). From this viewpoint, as an anion denoted as Y, especially bis(trifluoromethylsulfonyl)imide, trifluoroacetate and dimethylphosphate are preferably used.

The cation in a compound represented by the formula (1) is an ammonium ion or phosphonium ion. Among these, a phosphonium ion is preferably used from the viewpoint of the height of the catalytic power and the lowness of the viscosity.

In the case where a compound represented by the formula (1) is a phosphonium salt, specific examples of the compound include the following.

Trimethylhexylphosphonium bis(trifluoromethylsulfonyl) imide, trimethylhexylphosphonium bis(fluorosulfonyl) imide, trimethylhexylphosphonium dicyanamide, trimethyloctylphosphonium bis(trifluoromethylsulfonyl)imide, trimethyloctylphosphonium bis(fluorosulfonyl)imide, and trimethyloctylphosphonium dicyanamide.

Triethylbutylphosphonium bis(trifluoromethylsulfonyl) imide, triethylbutylphosphonium bis(fluorosulfonyl)imide, and triethylbutylphosphonium dicyanamide.

Triethylpentylphosphonium bis(trifluoromethylsulfonyl) imide, triethylpentylphosphonium bis(fluorosulfonyl)imide, and triethylpentylphosphonium dicyanamide.

Triethyloctylphosphonium chloride, triethyloctylphosphonium tetrafluoroborate, triethyloctylphosphonium hexafluorophosphate, triethyloctylphosphonium trifluoromethanesulfonate, triethyloctylphosphonium methanesulfonate, triethyloctylphosphonium trifluoroacetate, triethyloctylphosphonium bis(trifluoromethylsulfonyl)imide, triethyloctylphosphonium bis(fluorosulfonyl)imide, triethyloctylphosphonium dicyanamide, triethyloctylphosphonium thiocyanate, and triethyloctylphosphonium dimethylphosphate.

Triethyldodecylphosphonium chloride, triethyldodecylphosphonium tetrafluoroborate, triethyldodecylphosphonium trifluoromethanesulfonate, triethyldodecylphosphonium bis(trifluoromethylsulfonyl)imide, triethyldodecylphosphonium bis(fluorosulfonyl)imide, and triethyldodecylphosphonium dicyanamide.

Tributylmethylphosphonium chloride, tributylmethylphosphonium tetrafluoroborate, tributylmethylphosphonium trifluoromethanesulfonate, tributylmethylphosphonium bis(trifluoromethylsulfonyl)imide, tributylmethylphosphonium bis(fluorosulfonyl)imide, tributylmethylphosphonium dicyanamide, and tributylmethylphosphonium dimethylphosphate.

Tetrabutylphosphonium dimethylphosphate, tetrabutylphosphonium diethylphosphorodithioate, and tetrabuthylphosphonium amino acid salts.

Tributyloctylphosphonium tetrafluoroborate, tributyloctylphosphonium trifluoromethanesulfonate, tributyloctylphosphonium methanesulfonate, tributyloctylphosphonium trifluoroacetate, tributyloctylphosphonium bis(trifluoromethylsulfonyl)imide, tributyloctylphosphonium bis(fluorosulfonyl)imide, tributyloctylphosphonium dicyanamide, tributyloctylphosphonium thiocyanate, and tributyloctylphosphonium dimethylphosphate.

Tributyldodecylphosphonium tetrafluoroborate, tributyldodecylphosphonium trifluoromethanesulfonate, tributyldodecylphosphonium bis(trifluoromethylsulfonyl)imide, tributyldodecylphosphonium bis(fluorosulfonyl)imide, and tributyldodecylphosphonium dicyanamide.

Tributylhexadecylphosphonium trifluoromethanesulfonate, tributylhexadecylphosphonium bis(trifluoromethylsulfonyl)imide, tributylhexadecylphosphonium bis(fluorosulfonyl)imide, and tributylhexadecylphosphonium dicyanamide.

Trihexylmethylphosphonium tetrafluoroborate, trihexylmethylphosphonium trifluoromethanesulfonate, trihexylmethylphosphonium bis(trifluoromethylsulfonyl)imide, trihexylmethylphosphonium bis(fluorosulfonyl)imide, trihexylmethylphosphonium thiocyanate, trihexylmethylphosphonium dimethylphosphate, trihexylmethylphosphonium trifluoroacetate, and trihexylmethylphosphonium dicyanamide.

Trihexyltetradecylphosphonium tetrafluoroborate, trihexyltetradecylphosphonium trifluoromethanesulfonate, trihexyltetradecylphosphonium bis(trifluoromethylsulfonyl)imide, trihexyltetradecylphosphonium bis(fluorosulfonyl)imide, trihexyltetradecylphosphonium thiocyanate, trihexyltetradecylphosphonium dimethylphosphate, trihexyltetradecylphosphonium trifluoroacetate, and trihexyltetradecylphosphonium dicyanamide.

Trioctylmethylphosphonium tetrafluoroborate, trioctylmethylphosphonium trifluoromethanesulfonate, trioctylmethylphosphonium bis(trifluoromethylsulfonyl)imide, trioctylmethylphosphonium bis(fluorosulfonyl)imide, trioctylmethylphosphonium thiocyanate, trioctylmethylphosphonium dimethylphosphate, trioctylmethylphosphonium trifluoroacetate, and trioctylmethylphosphonium dicyanamide.

Trioctylethylphosphonium tetrafluoroborate, trioctylethylphosphonium trifluoromethanesulfonate, trioctylethylphosphonium bis(trifluoromethylsulfonyl)imide, trioctylethylphosphonium bis(fluorosulfonyl)imide, trioctylethylphosphonium thiocyanate, trioctylethylphosphonium dimethylphosphate, trioctylethylphosphonium trifluoroacetate, and trioctylethylphosphonium dicyanamide.

Among these phosphonium salts, particularly from the viewpoint of low viscosities at 80° C., preferably used are triethylpentylphosphonium bis(trifluoromethylsulfonyl)imide, tributylmethylphosphonium dimethylphosphate, triethylpentylphosphonium dicyanamide, triethyloctylphosphonium bis(trifluoromethylsulfonyl)imide, triethyldodecylphosphonium bis(trifluoromethylsulfonyl)imide, tributylmethylphosphonium bis(trifluoromethylsulfonyl)imide, tetrabuthylphosphonium diethylphosphorodithioate, tributyloctylphosphonium trifluoromethanesulfonate, tributyloctylphosphonium trifluoroacetate, tributyloctylphosphonium bis(trifluoromethylsulfonyl)imide, tributyloctylphosphonium dicyanamide, tributyloctylphosphonium thiocyanate, tributyldodecylphosphonium bis(fluorosulfonyl)imide, trihexylmethylphosphonium bis(trifluoromethylsulfonyl)imide, and trioctylmethylphosphonium bis(trifluoromethylsulfonyl)imide.

A compound represented by the formula (1), for example, a quaternary phosphonium salt, can be prepared by mixing a tertiary phosphine, and an alkyl halide or a dialkylsulfuric acid or the like, and as required, heating the mixture. In the case of preparing a quaternary phosphonium salt having a variously different anion, the quaternary phosphonium salt may be prepared in such a way that a quaternary phosphonium halide (chloride, bromide, or iodide) is dissolved in an aqueous medium, and allowed to react with a reagent to generate an anion species to exchange the anions.

In the case of a quaternary ammonium salt, as in the case of a quaternary phosphonium salt, a tertiary amine, and an alkyl halide or a dialkylsulfuric acid or the like are mixed, and as required, heated to make a quaternary ammonium halide salt. Then, the obtained quaternary ammonium halide salt is dissolved in an aqueous medium such as water, and allowed to react with a regent to generate an anion species such as hydroborofluoric acid or tetrafluorophosphoric acid to exchange the anions, whereby the quaternary ammonium salt can be prepared.

The use amount of a catalyst in the first step is preferably 0.05 to 20 g, especially 0.5 to 10 g, with respect to 1 mol of a phosphorous acid triester. As other reaction conditions in the first step, the temperature is preferably −10 to 90° C. The pressure may usually be atmospheric pressure, but the reaction may be carried out under a higher or reduced pressure with no trouble. The reaction time is suitably regulated according to the kinds of raw materials and the reaction temperature. Generally, a low reaction temperature needs a long time, and a high one can complete the reaction in a short time. The reaction time is usually 0.5 to 80 hours, and especially preferably 2 to 24 hours.

In the first step, a solvent may be used, or may not be used depending on the kinds of raw materials and a catalyst. In the case of using a solvent, an inactive solvent which does not react with the raw materials, the catalyst and the reaction product is preferably used. Examples of such solvents include aromatic hydrocarbons such as benzene, chlorobenzene, toluene and xylene, paraffinic hydrocarbons such as hexane, pentane, heptane, octane and nonane, and petroleum hydrocarbons such as kerosine and ligroin. These solvents may be used singly or in combination of two or more.

In the first step, a catalyst is dissolved or dispersed in a phosphorous acid triester; and phosphorus trichloride is added thereto, and thereafter the reaction is carried out at a predetermined temperature for a predetermined time. In this case, the order of addition of the phosphorous acid triester and phosphorus trichloride may be changed. The reaction in the first step is preferably carried out in the absence of water. The absence of water in the reaction system can hardly weaken the effect of use of a catalyst. Further, the absence of water hardly permits production of a phosphorous acid diester which would be generated by decomposition of a phosphorous acid triester caused by the presence of water. This is advantageous from the viewpoint of obtaining a high-purity chlorophosphite.

In the second step, the chlorophosphite and the catalyst are separated from the reaction liquid containing the chlorophosphite obtained in the first step. The separation of the both is carried out by vaporizing the reaction liquid in a short time. The employment of such a separation process prevents the chlorophosphite as a target substance from being heated for a long time in the state that the chlorophosphite contacts with the catalyst, and the chlorophosphite thereby hardly becomes susceptible to secondary decomposition by the catalyst. Consequently, a high-purity chlorophosphite can be obtained in a high yield.

In the second step, means to separate the chlorophosphite and the catalyst from the reaction liquid containing the chlorophosphite uses a thin film distillation unit industrially advantageously from the viewpoint of being capable of continuously carrying out the second step. With respect to the thin film distillation unit, a thin film distillation unit equipped with means to heat a reaction liquid containing a chlorophosphite to vaporize the chlorophosphite, and means to cool and liquefy the vaporized chlorophosphite is preferable from the viewpoint of being capable of efficiently separating a catalyst and the chlorophosphite; and a thin film distillation unit of a natural flow-down type is especially preferably used from the viewpoint of being capable of providing a very high-purity chlorophosphite.

FIG. 1(a) shows schematically a separation unit 10 used in the second step. The separation unit 10 is equipped with a thin film distillation unit 20 as shown in FIG. 1(a). FIG. 1(b) is a schematic diagram of a cross-section taken on line b-b of the thin film distillation unit 20 in FIG. 1(a). As shown in the FIGURE, the thin film distillation unit 20 is equipped with an inner tube 21 and a jacket 22 each extending in the same direction. The inner tube 21 is arranged in the jacket 22. A space S1 is formed between the inner tube 21 and the jacket 22. The inner tube 21 and the jacket 22 are composed of, for example, a glass or a metal.

A cooling medium is circulated in a space S2 in the inner tube 21 in the thin film distillation unit 20. The outer surface 21a of the inner tube 21 is thereby cooled to a predetermined temperature. On the other hand, a heating medium is circulated in a space S3 in the jacket 22. The inner wall surface 22a of the jacket 22 is thereby heated to a predetermined temperature.

Giving an explanation of the second step using the separation unit 10 having such a structure, the reaction liquid obtained in the first step is fed from an upper part of the thin film distillation unit 20. The reaction liquid is fed so as to flow down in a filmy state on the inner wall surface 22a of the jacket 22. Since the reaction liquid flows down in a filmy state on the inner wall surface 22a, the reaction liquid is rapidly heated. The chlorophosphite, which is a low-boiling point component, is thereby vaporized in a short time. By contrast, since the catalyst has a higher boiling point than the chlorophosphite, it does not vaporize and continues to flow down on the inner wall surface 22a of the jacket 22. From the viewpoint of securing this operation, it is important that the heating temperature of the inner wall surface 22a of the jacket 22 by the circulation of the heating medium is a temperature equal to or higher than the vaporization temperature of the chlorophosphite, and is a temperature at which the catalyst does not vaporize. In order for the chlorophosphite to vaporize at a low temperature, the interior of the thin film distillation unit 20 may be under reduced pressure. In order to promote the vaporization of the chlorophosphite and make a uniform film, the inner wall surface 22a may be rotated about the axis as it is.

The vaporized chlorophosphite contacts with the outer surface 21a of the inner tube 21 located inside the jacket 22. Since the outer surface 21a is cooled as described above, the chlorophosphite having contacted with the outer surface 21a is cooled and liquefied on the outer surface 21a. Then, the liquefied chlorophosphite flows down on the outer surface 21a. From this viewpoint, it is important that the cooling temperature of the outer surface 21a of the inner tube 21 by the circulation of the cooling medium is a temperature equal to or lower than the liquefying temperature of the chlorophosphite. Especially the cooling temperature is made preferably a temperature at which the chlorophosphite having been vaporized in a short time is liquefied and the liquefied chlorophosphite exhibits a fluidity, from the viewpoint of providing a target substance in a high yield, and the temperature is 0° C. or lower in many cases, preferably −100 to 0° C., and especially preferably −30° C. to −5° C. In order to promote the liquefaction of the chlorophosphite, the inner tube 21a may be rotated about its axis.

By using the separation unit 10 in such a way, the chlorophosphite flows down along the outer surface 21a of the inner tube 21, and on the other hand, the catalyst flows down along the inner wall surface 22a of the jacket 22. Consequently, the chlorophosphite and the catalyst can successfully be separated. Moreover, since a catalyst used in the present invention has a low viscosity as described before, the catalyst is hardly caused to adhere in a powdery or pasty state to the inner wall surface 22a of the jacket 22 due to the solidification. Consequently, the operation can be carried out continuously over a long time with no discontinuance, thus allowing a high yield. Since the efficiency of the separation of the chlorophosphite and the catalyst becomes good, a high-purity chlorophosphite can be provided in a high yield.

EXAMPLES

Hereinafter, the present invention will be described in detail by way of Examples. However, the scope of the present invention is not limited to such Examples.

Example 1

2.00 g of triethyloctylphosphonium bis(trifluoromethylsulfonyl)imide (the viscosity at 80° C.: 25 mPa·s) as a catalyst was dissolved in 37.90 g of triethyl phosphite to make a solution. 16.80 g of phosphorus trichloride was dropwise charged at 20 to 25° C. in the solution while the solution was being stirred. After the finish of the dropping, the reaction was carried out at 25 to 30° C. for 6 hours to produce diethyl chlorophosphite.

The reaction liquid containing the produced diethyl chlorophosphite was fed to the thin film distillation unit 20 of the separation unit 10 shown in FIG. 1. The interior of the thin film distillation unit 20 was made in a reduced pressure state of 5 kPa. A kerosine of −10° C. was circulated in the inner tube 21 of the thin film distillation unit 20 to cool the outer surface 21a. A silicone oil of 90° C. was circulated in the jacket 22 to heat the inner wall surface 22a at 80° C. The reaction liquid was fed continuously in the thin film distillation unit 20, and after 30 min, the feed of the liquid was stopped. As a result, 51.00 g of a liquid (the yield: 95.2%) having flowed down along the outer surface 21a of the inner tube 21 and 5.7 g of a liquid having flowed down along the inner wall surface 22a of the jacket 22 were obtained. The purity of diethyl chlorophosphite in the liquid having flowed down along the outer surface 21a of the inner tube 21 was measured, and was 82.6%. No adhesion of the catalyst due to the solidification thereof was observed in the thin film distillation unit 20.

Example 2

2.00 g of tributylmethylphosphonium dimethylphosphate (the viscosity at 80° C.: 34 mPa·s) as a catalyst was dissolved in 37.90 g of triethyl phosphite to make a solution. 16.80 g of phosphorus trichloride was dropwise charged at 20 to 25° C. in the solution while the solution was being stirred. After the finish of the dropping, the reaction was carried out at 25 to 30° C. for 3 hours to produce diethyl chlorophosphite. The yield of the diethyl chlorophosphite was 96.5% and the purity thereof was 88.2%. No adhesion of the catalyst due to the solidification thereof was observed in the thin film distillation unit 20.

Example 3

2.00 g of tributyloctylphosphonium trifluoromethanesulfonate (the viscosity at 80° C.: 52 mPa·s) as a catalyst was dissolved in 37.90 g of triethyl phosphite to make a solution. 16.80 g of phosphorus trichloride was dropwise charged at 20 to 25° C. in the solution while the solution was being stirred. After the finish of the dropping, the reaction was carried out at 25 to 30° C. for 8 hours to produce diethyl chlorophosphite. The yield of the diethyl chlorophosphite was 96.1% and the purity thereof was 84.7%. No adhesion of the catalyst due to the solidification thereof was observed in the thin film distillation unit 20.

Comparative Example 1

Diethyl chlorophosphite was obtained as in Example 1, except for using 2.0 g of tetra-n-butylphosphonium bromide (solid at 80° C.) in place of the catalyst used in Example 1. The yield of the diethyl chlorophosphite was 73.5% and the purity thereof was 71.3%. Adhesion of the catalyst due to the solidification thereof was observed in the thin film distillation unit 20.

INDUSTRIAL APPLICABILITY

The present invention can effectively prevent the adhesion of a catalyst to an evaporator in a process of separating a chlorophosphite as a target substance from a reaction liquid by evaporation. Consequently, the present invention can produce continuously a chlorophosphite, and can produce a high-purity chlorophosphite in a high yield.

BRIEF DESCRIPTION OF THE DRAWING

FIG. 1 is a schematic diagram illustrating a separation unit suitably used in a second step in the production process according to the present invention.

DESCRIPTION OF SYMBOLS

10 Separation unit
20 Thin film distillation unit
21 Inner tube
21a Outer surface
22 Jacket
22a Inner wall surface

The invention claimed is:

1. A process for producing a chlorophosphite, comprising:
a first step of allowing phosphorus trichloride and a phosphorous acid triester represented by $(RO)_3P$ (wherein R denotes an alkyl group, a substituted alkyl group, a phenyl group or a substituted phenyl group) to react in the presence of a catalyst having a viscosity at 80° C. of 100 mPa·s or lower to produce a reaction liquid containing a chlorophosphite represented by $RO(R')PCl$ (wherein R is the same as defined above, and R' denotes RO or a chlorine atom); and
a second step of vaporizing the reaction liquid containing the chlorophosphite obtained in the first step to separate the catalyst,
wherein the catalyst is a quaternary ammonium salt or quaternary phosphonium salt which is a liquid at 80° C.

2. The process for producing a chlorophosphite according to claim 1, wherein means to separate the catalyst by vaporizing the reaction liquid containing the chlorophosphite in the second step uses a thin film distillation unit.

3. The process for producing a chlorophosphite according to claim 2, wherein the thin film distillation unit comprises means to heat the reaction liquid containing the chlorophosphite to vaporize the chlorophosphite, and means to cool and liquefy the vaporized chlorophosphite.

4. The process for producing a chlorophosphite according to claim 2 or 3, wherein the thin film distillation unit is a thin film distillation unit of a natural flow-down type.

5. The process for producing a chlorophosphite according to claim 4, wherein the catalyst and the liquefied chlorophosphite are allowed to naturally flow down to be recovered.

6. The process for producing a chlorophosphite according to claim 1, wherein the catalyst is represented by formula (I) below:

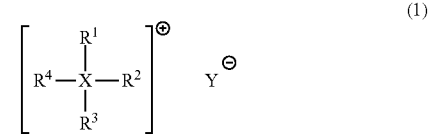

where, $R^1$, $R^2$, $R^3$ and $R^4$ each independently denote an alkyl group having 1 to 14 carbon atoms; X denotes N or P; and Y denotes a monovalent anion.

7. The process for producing a chlorophosphite according to claim 6, wherein Y is bis(trifluoromethylsulfonyl)imide, bis(fluorosulfonyl)imide, dicyanamide, halogens, tetrafluoroborate, hexafluorophosphate, trifluoromethanesulfonate, methanesulfonate, trifluoroacetate, thiocyanate, dimethylphosphate, or amino acids.

8. The process for producing a chlorophosphite according to claim 7, wherein Y is bis(trifluoromethylsulfonyl)imide, trifluoromethanesulfonate, trifluoroacetate, dimethylphosphate.

* * * * *

UNITED STATES PATENT AND TRADEMARK OFFICE
CERTIFICATE OF CORRECTION

PATENT NO. : 8,357,822 B2
APPLICATION NO. : 12/745109
DATED : January 22, 2013
INVENTOR(S) : Sasaki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this
First Day of September, 2015

Michelle K. Lee
*Director of the United States Patent and Trademark Office*